US012017860B2

(12) United States Patent
Yagi et al.

(10) Patent No.: US 12,017,860 B2
(45) Date of Patent: Jun. 25, 2024

(54) SHEET MATERIAL CONVEYANCE DEVICE AND DISPOSABLE WEARING ARTICLE MANUFACTURING SYSTEM PROVIDED WITH SAID CONVEYANCE DEVICE

(71) Applicant: ZUIKO CORPORATION, Osaka (JP)

(72) Inventors: Hiroaki Yagi, Osaka (JP); Yukihiko Fujita, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 110 days.

(21) Appl. No.: 17/800,836

(22) PCT Filed: Feb. 5, 2021

(86) PCT No.: PCT/JP2021/004302
§ 371 (c)(1),
(2) Date: Aug. 18, 2022

(87) PCT Pub. No.: WO2021/171963
PCT Pub. Date: Sep. 2, 2021

(65) Prior Publication Data
US 2023/0080034 A1    Mar. 16, 2023

(30) Foreign Application Priority Data

Feb. 29, 2020   (JP) ................. 2020-034483

(51) Int. Cl.
*B65G 17/48* (2006.01)
*A61F 13/15* (2006.01)
(Continued)

(52) U.S. Cl.
CPC ........ *B65G 17/48* (2013.01); *A61F 13/15764* (2013.01); *B65G 17/34* (2013.01);
(Continued)

(58) Field of Classification Search
CPC ...... B65G 17/14; B65G 47/244; B65G 54/02; B65G 17/48; B65G 17/34;
(Continued)

(56) References Cited

U.S. PATENT DOCUMENTS

| 10,106,339 B2* | 10/2018 | Prüssmeier | ............ B65G 35/06 |
| 2001/0003188 A1* | 6/2001 | Kikinis | .................. H04L 45/42 |
| | | | 348/E5.008 |

FOREIGN PATENT DOCUMENTS

| CN | 106115343 A | 11/2016 |
| EP | 1152726 A1 | 11/2001 |

(Continued)

OTHER PUBLICATIONS

International Search Report for corresponding Application No. PCT/JP2021/004302, mailed Mar. 30, 2021.
(Continued)

*Primary Examiner* — James R Bidwell
(74) *Attorney, Agent, or Firm* — Renner, Otto, Boisselle & Sklar, LLP

(57) ABSTRACT

A conveying device for conveying a sheet-like material of the present invention includes: a rail portion arranged in a loop shape; a plurality of travelers; a linear motor for circulating the travelers along the rail portion; and a pad attached to each of the travelers, wherein the pad circulates in at least one horizontal plane while holding the sheet-like material on the pad, thereby conveying the sheet-like material.

20 Claims, 6 Drawing Sheets

(51) Int. Cl.
　　　*B65G 17/34*　　　(2006.01)
　　　*B65G 47/244*　　(2006.01)
　　　*B65G 54/02*　　　(2006.01)
(52) U.S. Cl.
　　　CPC ............ *B65G 47/244* (2013.01); *B65G 54/02* (2013.01); *B65G 2201/0229* (2013.01); *B65G 2811/095* (2013.01)
(58) Field of Classification Search
　　　CPC ....... B65G 2201/0229; B65G 2811/095; A61F 13/15764
　　　USPC .......................................................... 198/805
　　　See application file for complete search history.

(56) References Cited

U.S. PATENT DOCUMENTS

| | | |
|---|---|---|
| 2013/0140755 A1 | 6/2013 | Ninomiya et al. |
| 2014/0331888 A1 | 11/2014 | Wernersbach et al. |
| 2015/0107959 A1* | 4/2015 | Engelhardt ............ B65G 54/02 198/377.01 |
| 2019/0055091 A1* | 2/2019 | Achterberg .......... B65G 47/244 |
| 2019/0060134 A1 | 2/2019 | Piantoni et al. |
| 2020/0002040 A1* | 1/2020 | von Birgelen ......... B65G 23/23 |
| 2020/0347861 A1 | 11/2020 | Honge |

FOREIGN PATENT DOCUMENTS

| | | |
|---|---|---|
| JP | 2012-011048 A | 1/2012 |
| JP | 6617249 B1 | 12/2019 |
| WO | 2017/158572 A1 | 9/2017 |
| WO | 2019/098066 A1 | 5/2019 |

OTHER PUBLICATIONS

Extended European Search Report for corresponding EP Application No. 21760895.9 dated Oct. 20, 2023.

* cited by examiner

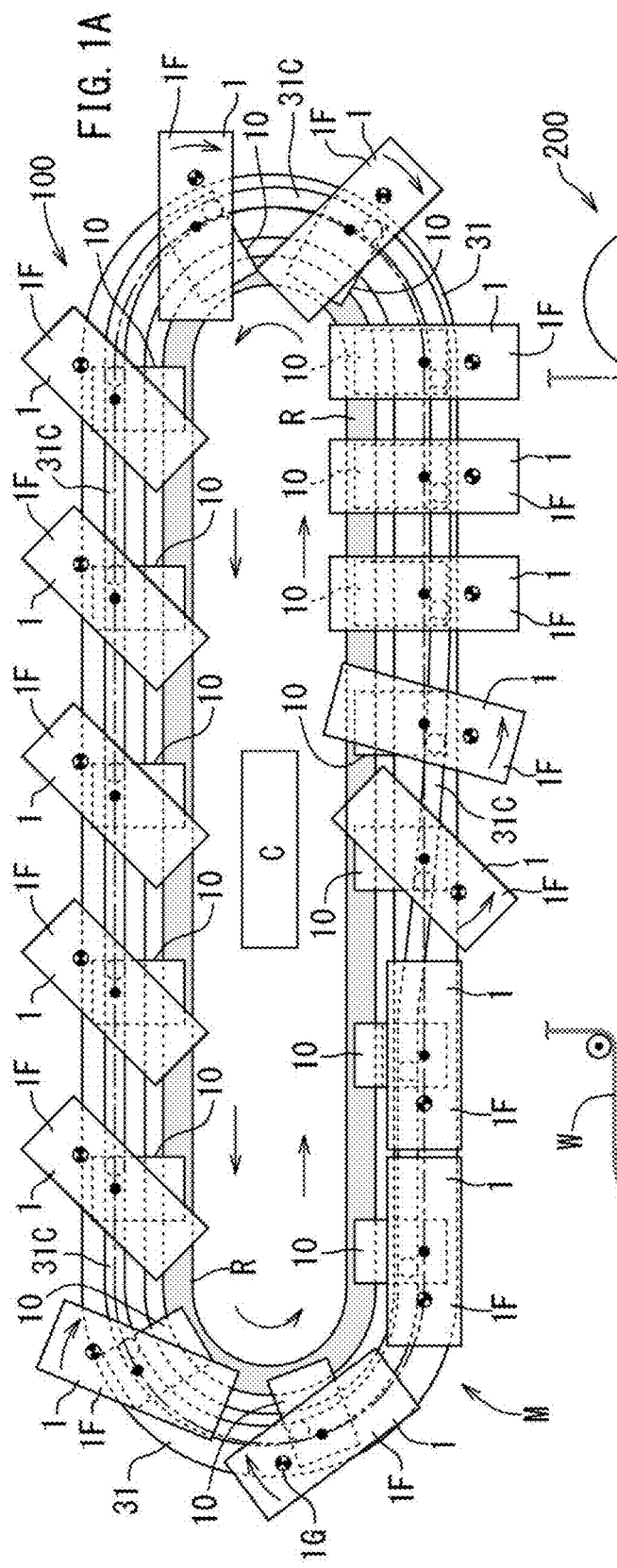
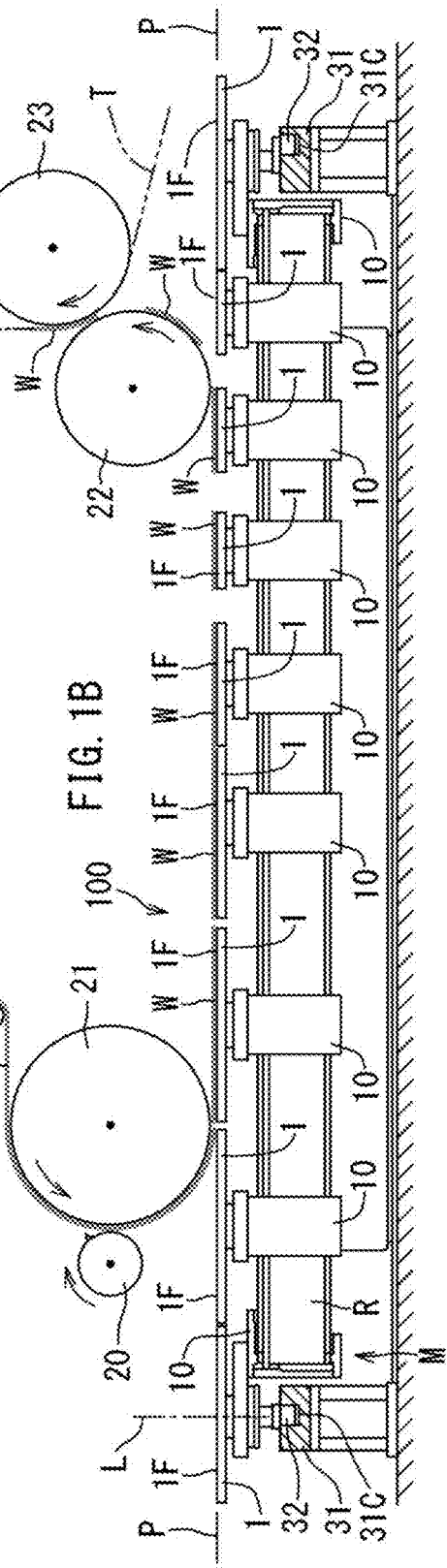
FIG. 1A
FIG. 1B

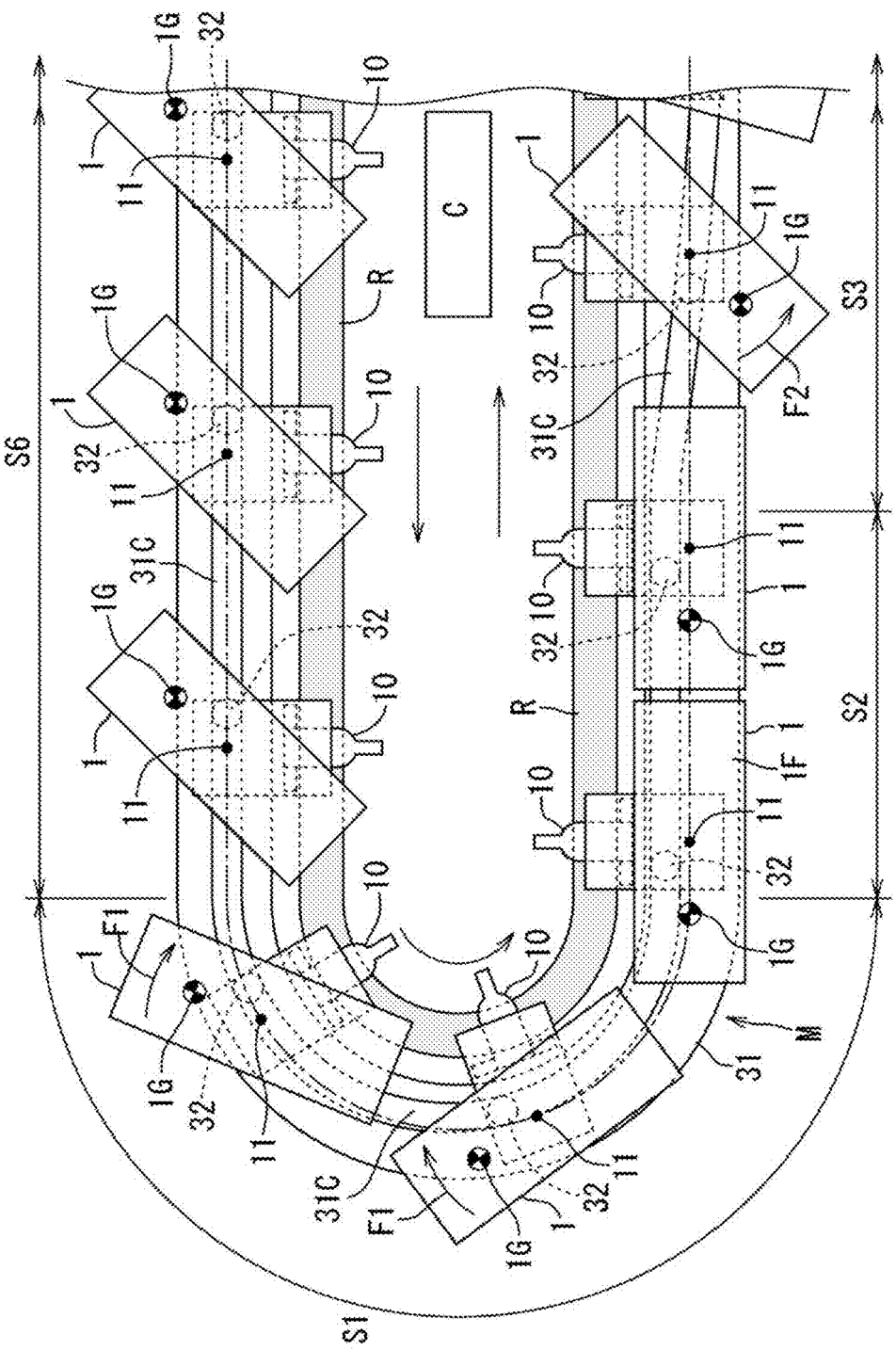

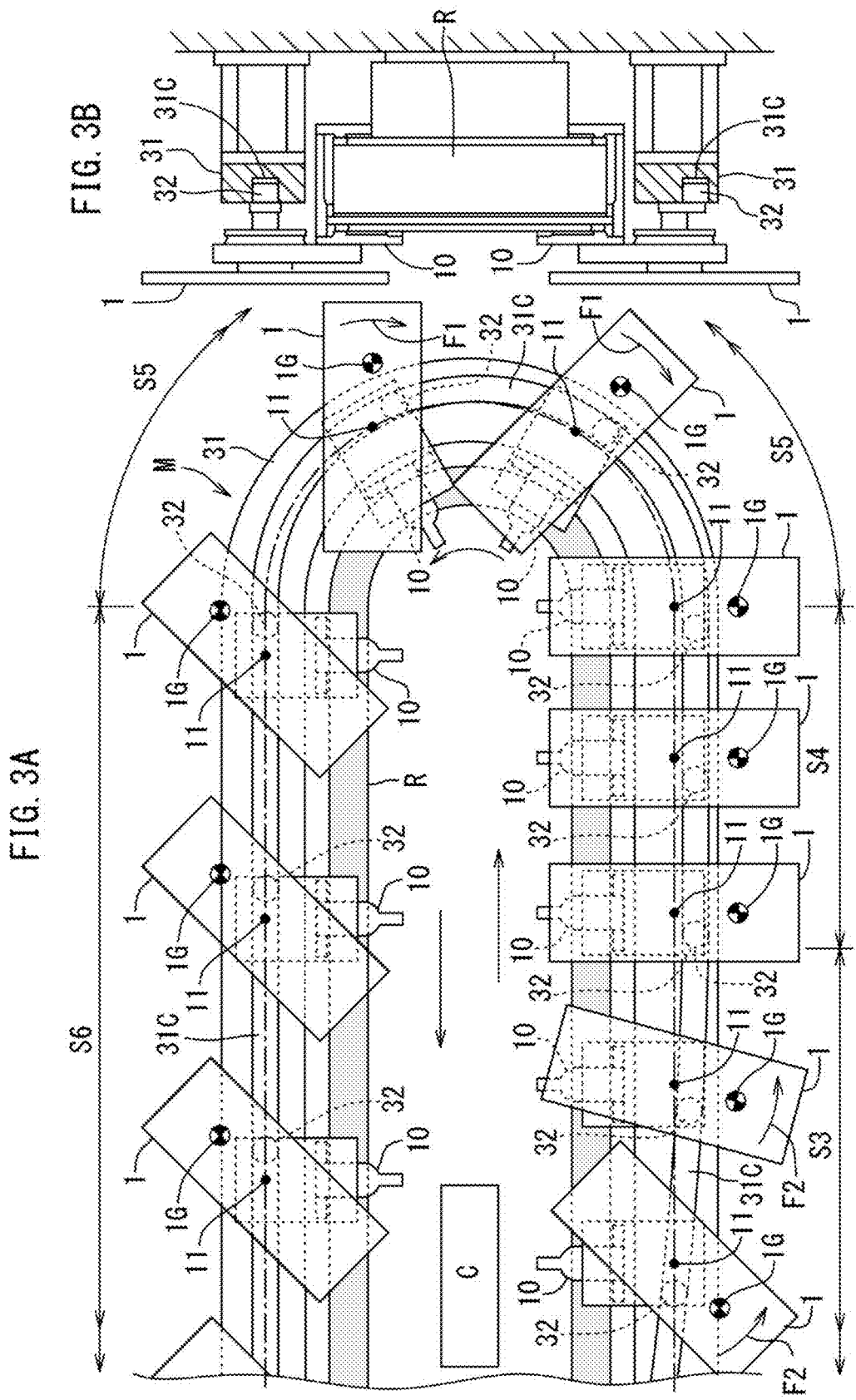

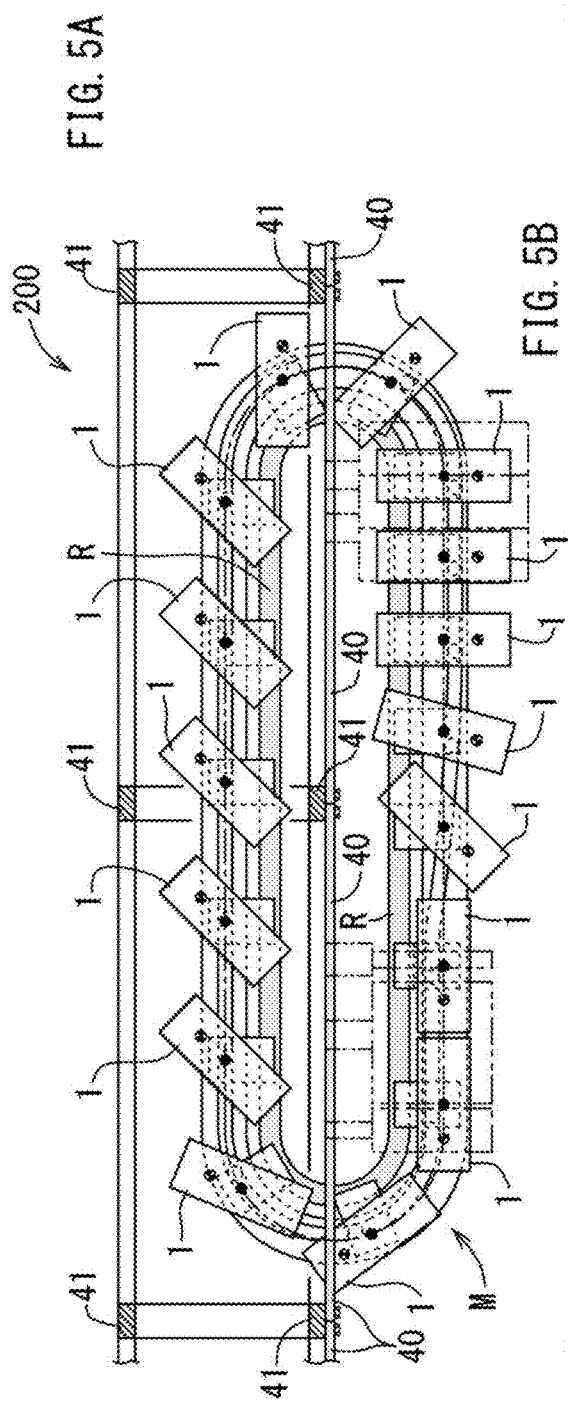
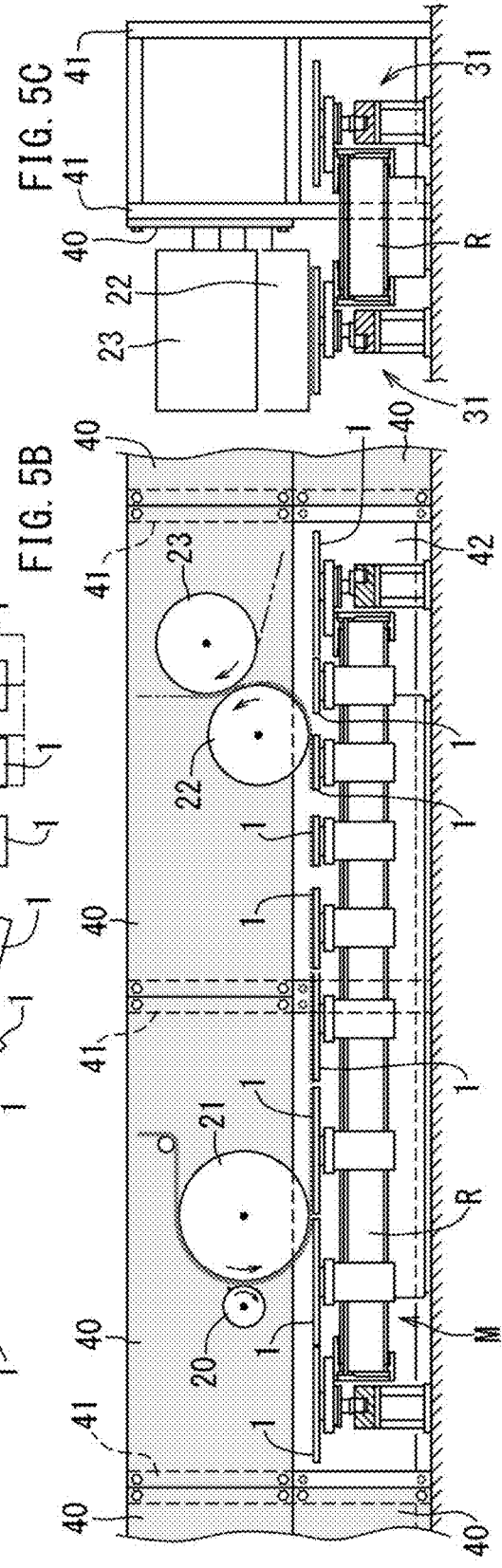

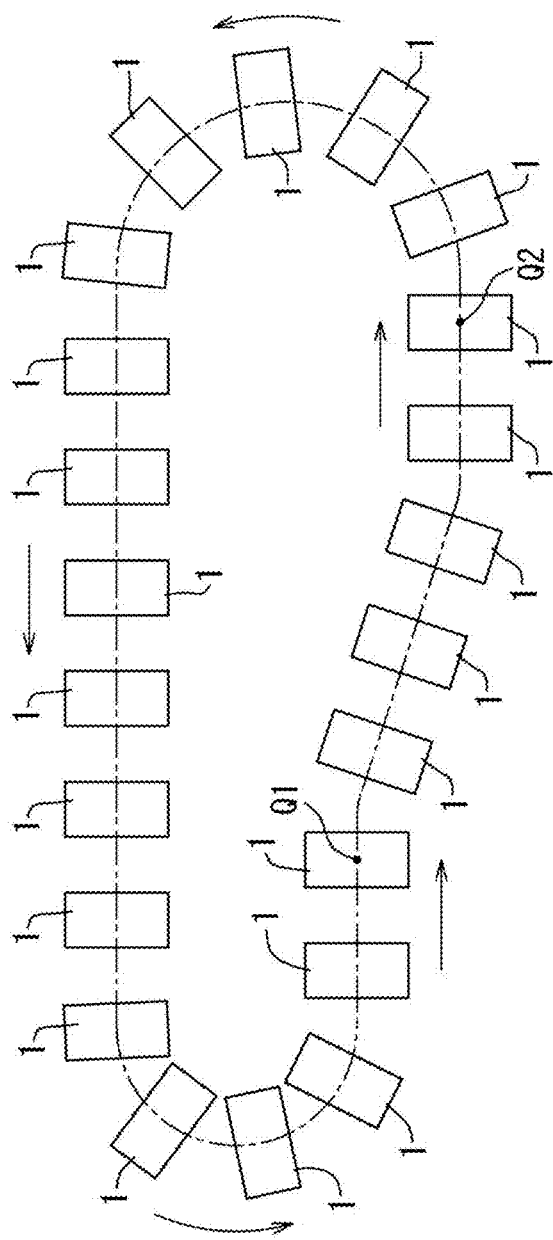

SHEET MATERIAL CONVEYANCE DEVICE AND DISPOSABLE WEARING ARTICLE MANUFACTURING SYSTEM PROVIDED WITH SAID CONVEYANCE DEVICE

TECHNICAL FIELD

This invention relates to a conveying device for conveying a sheet-like material and a system for manufacturing disposable worn articles (wearing articles) having the same conveying device.

BACKGROUND ART

As a conveying device of this type, one using a linear motor is known in the art (the first patent document). This conventional conveying device includes a traveler that circulates around a horizontal axis along a loop-shaped rail portion and a pad provided on the outer circumference of the traveler.

CITATION LIST

Patent Document

[FIRST PATENT DOCUMENT] WO 2017/158572 A1 (abstract)

SUMMARY OF INVENTION

However, with the conventional technique described above, the position of said pad moves in the vertical direction over one revolution of the pad along the rail portion. Therefore, a large load is applied to the linear motor at the uphill portion of the rail portion.

Moreover, the rail portion is configured so that the traveler circulates around the horizontal axis, and thus the rail portion tends to become larger in the height direction.

Thus, it is an object of the present invention to provide a device for conveying a sheet-like material, with which it is possible to suppress the load on the linear motor and to realize a smaller size in the height direction (vertical direction).

A conveying device 100 for conveying a sheet-like material according to the present invention includes: a rail portion R arranged in a loop shape; a plurality of travelers 10; a linear motor M for circulating the travelers 10 along the rail portion R; and a pad 1 attached to each of the travelers 10, wherein the pad 1 circulates in at least one horizontal plane P while holding the sheet-like material W on the pad 1, thereby conveying the sheet-like material W.

According to the present invention, the pad conveying the sheet-like material circulates in at least one horizontal plane. Therefore, the pad does not rise in the height direction (vertical direction), and it is possible to suppress the load on the linear motor.

Since the pad circulates along one horizontal plane, it is unlikely for the rail portion to become larger in the height direction (it can be reduced in size).

Note that "along one horizontal plane" means that there may be slight slopes or undulations as long as it is generally horizontal.

BRIEF DESCRIPTION OF THE DRAWINGS

FIG. 1A is a schematic plan view of a conveying device showing one embodiment of the present invention, and FIG. 1B is a front view thereof.

FIG. 2 is a schematic plan view showing the left half of the conveying device.

FIG. 3A is a schematic plan view showing the right half of the conveying device, and FIG. 3B is a right side view of the conveying device.

FIG. 5A, FIG. 5B and FIG. 5C are a plan sectional view, a front view and a transverse sectional view, respectively, showing the state where the conveying device is assembled in a frame.

FIG. 6 is a plan view showing the orbit of a pad according to another embodiment.

Figure 4:
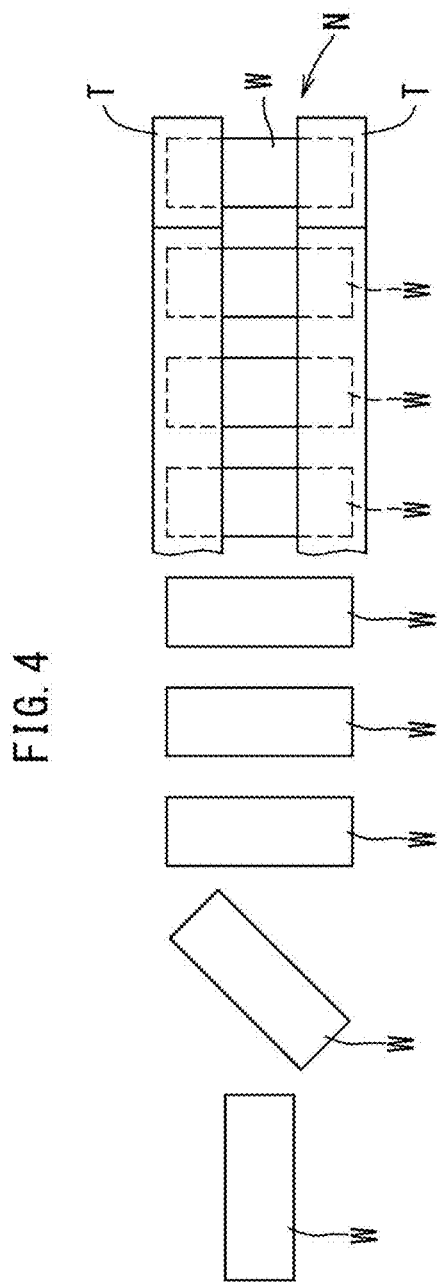
FIG. 4 is a plan view showing one embodiment of a method for manufacturing a worn article.

Note that the sheet-like material is colored in gray in these figures.

DESCRIPTION OF EMBODIMENTS

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Embodiments of the present invention will now be described with reference to the drawings.

FIG. 1A is a schematic view of a conveying device 100, which is one embodiment of the present invention, and FIG. 1B is a schematic view of a manufacturing system 200 for manufacturing a disposable worn article N including the conveying device 100.

As shown in FIG. 1A, the conveying device 100 includes the rail portion R, the plurality of travelers 10, a linear motor M and a pad 1. As also shown in FIG. 1B, the present manufacturing system 200 includes the conveying device 100, a first roll 21, a second roll 22, etc. The present manufacturing system 200 manufactures a well-known disposable worn article N by providing an absorbent body, which is the sheet-like material W, so as to bridge between a pair of around-torso portions T, as shown in FIG. 4.

The absorbent body, which is a type of the sheet-like material W, may include, for example, an absorbent core sandwiched between a top sheet and a back sheet. The around-torso portion T may have an elastic member such as rubber threads. The disposable worn article N may be a disposable diaper or pants.

In FIG. 1A, the linear motor M circulates the travelers 10 along the rail portion R arranged in a loop shape. Such a linear motor M may be, for example, the structure disclosed in US 2014/331888 A1, the entire disclosure of which is hereby incorporated by reference.

The pad 1 is attached to each of the travelers 10. As shown in FIG. 1B, each pad 1 circulates in one horizontal plane P while holding the sheet-like material W and conveying the sheet-like material W.

The first roll 21 contacts the holding surface 1F of the pad 1 with the sheet-like material W therebetween while holding the sheet-like material W to place (hand over) the sheet-like material W on the holding surface 1F. Specifically, the first roll 21 sucks and holds the strip-shaped sheet-like material W conveyed from upstream of the first roll 21 on the outer circumference of the first roll 21, and releases the suction state upon contacting the holding surface 1F of the pad 1 so that it is easier to place the strip-shaped sheet-like material W on the holding surface 1F.

The second roll 22 contacts the holding surface 1F with the sheet-like material W on the pad 1 therebetween to receive the sheet-like material W from the holding surface 1F.

In FIG. 1B, the first roll 21 intermittently contacts the cutter 20 that cuts the strip-shaped sheet-like material W. On the other hand, the second roll 22 places the sheet-like material W, which has been received from the holding surface 1F of the pad 1, on the strip-shaped around-torso portion T on a third roll 23.

In this embodiment, as shown in FIG. 1A and FIG. 1B, each pad 1 is attached to the traveler 10 so that the pad 1 can change its attitude by rotating around the axis L, which is orthogonal to one horizontal plane P. Note that for the sake of illustration, the axis L of FIG. 1B is only drawn on one pad 1. For example, each pad 1 of FIG. 1A rotates 90° forward/reverse around the axis center 11 (FIG. 2), which is indicated by a black circle, during one revolution around the rail portion R.

In the present embodiment, the conveying device 100 includes a controller C that controls the linear motor M. As shown in FIG. 2 and FIG. 3, the rail portion R includes an acceleration section S1, a high speed section S2 downstream of the acceleration section S1 and adjacent to the acceleration section S1, a deceleration section S3 downstream of the high speed section S2 and adjacent to the high speed section S2, and a low speed section S4 downstream of the deceleration section S3 and adjacent to the deceleration section S3. The controller C controls the travel of the traveler 10 via the linear motor M as follows.

In the first acceleration section S1 of FIG. 2, the linear motor M accelerates the traveler 10. In the high speed section S2 downstream of the first acceleration section S1, the linear motor M makes the traveler 10 travel at a constant high speed. In the deceleration section S3 downstream of the high speed section S2, the linear motor M decelerates the traveler 10.

In the low speed section S4 downstream of the deceleration section S3 of FIG. 3A, the linear motor M causes the traveler 10 to travel at a constant low speed. In the second acceleration section S5 downstream of the low speed section S4, the linear motor M again accelerates the traveler 10. In the constant speed section S6 downstream of the second acceleration section S5, the linear motor M makes the traveler 10 travel at a constant speed.

As shown in FIG. 1A, a loop-shaped guide 31 is arranged around the outer circumference of the rail portion R. The guide 31 of FIG. 1B includes a cam groove 31C to change and control the attitude of the pad 1 during the circulation.

Note that in order to make the guide 31 and the rail portion R easier to see, the area corresponding to the surface of the rail portion R is colored in gray in FIG. 1A, FIG. 2 and FIG. 3A.

As shown in FIG. 1B and FIG. 3B, cam followers (guided portions) 32 are fitted into the cam groove 31C. A cam follower 32 of FIG. 1B is provided for each pad 1 and is guided in the cam groove 31C (FIG. 3B). As shown in FIG. 2 and FIG. 3A, in each pad 1, each cam follower 32 is slightly eccentric with respect to the axis center 11 (black circle), thereby controlling the attitude change of the pad 1.

In FIG. 1A, FIG. 2, FIG. 3A and FIG. 5A, the center of gravity 1G of the pad 1 is indicated by a circle colored in black/white. The center of gravity 1G is located at a position that is substantially eccentric with respect to the axis center 11 of the pad 1. That is, the center of gravity 1G of the pad 1 is set at a position that is substantially away from the axis L (FIG. 1B).

Due to the eccentricity of the center of gravity 1G, as the traveler 10 is accelerated/decelerated as described above, an inertial force acts on each pad 1 around the axis L (FIG. 1B), thus causing the pad 1 to swivel (pivot) around the axis L.

The eccentricity of the center of gravity 1G and the inertial force acting on the pad 1 due to the acceleration/deceleration of the traveler 10 will now be described.

In the first acceleration section S1 of FIG. 2, the rail portion R is semi-circular arc-shaped, the axis center 11 of the pad 1 is accelerated, the center of gravity 1G obliquely rearward of the axis center 11 in the direction of travel lags behind the axis center 11, and the inertia force acts on the pad 1 in the first rotation direction F1 so that the pad 1 swivels slightly in the first rotation direction F1. The inertia force reduces the contact pressure of the cam follower 32 contacting the guide 31, which reduces the load on the linear motor M. At the same time, the cam follower 32 is guided by the cam groove 31C and the attitude of the pad 1 takes a first attitude that is elongated along the direction of travel, as shown in the following high speed section S2.

In the high speed section S2, the pad 1 travels at a high speed while maintaining the first attitude, and the pads 1, 1 adjacent to each other come closest to each other. In other words, the short side of the preceding pad 1 and the short side of the following pad 1 are facing each other. In the high speed section S2, the rail portion R is straight.

When the pad 1 of FIG. 2 enters the deceleration section S3 from the high speed section S2, the cam follower 32 is guided by the cam groove 31C so that the pad 1 and the center of gravity 1G start to swivel in the second rotation direction F2 around the axis center 11.

On the other hand, in the deceleration section S3, the pad 1 is decelerated and the inertia force that urges the center of gravity 1G to proceed ahead of the axis center 11 acts in the second rotation direction F2 to promote smooth rotation of the pad 1. That is, the contact pressure with which the cam follower 32 contacts the guide 31 decreases, thereby reducing the load on the linear motor M. Note that the second rotation direction F2 is opposite to the first rotation direction F1.

When the pad 1 of FIG. 3A enters the low speed section S4 from the deceleration section S3, the attitude of the pad 1 takes a second attitude that is short in the direction of travel. The deceleration section S3 and the low speed section S4 are in the same straight line as the high speed section S2 (FIG. 2). In the low speed section S4, the distance between the centers of gravity 1G of the pads 1 adjacent to each other decreases, but there is a gap between the pads 1. Note that the second attitude is an attitude that is obtained as the pad 1 swivels 90° from the first attitude of FIG. 2.

When the pad 1 of FIG. 3A enters the second acceleration section S5 from the low speed section S4, the pad 1 is accelerated again. In the second acceleration section S5, the rail portion R is semi-circular arc-shaped.

In the second acceleration section S5, the inertia force again acts on the center of gravity 1G of the accelerated pad 1 in the first rotation direction F1, and the pad 1 starts swiveling in the first rotation direction F1. At the same time, in the second acceleration section S5, the cam follower 32 is guided by the cam groove 31C to control the attitude of the pad 1.

When the pad 1 of FIG. 3A enters the constant speed section S6 from the second acceleration section S5, the pad 1 travels at a constant speed. In the constant speed section S6, the rail portion R is straight. In the constant speed section S6, the attitude of the pad 1 is constant and the pad 1 travels while remaining in an attitude that is inclined oblique to the rail portion R. In the constant speed section S6, the center of gravity 1G is located obliquely rearward of the axis center 1l in the direction of travel.

When the pad 1 of FIG. 2 enters the first acceleration section S1 again from the constant speed section S6, the speed of the pad 1 is accelerated. The behavior of the pad 1 in the acceleration section S1 is as described above.

Next, how the sheet-like material W of FIG. 1B is conveyed will be described.

The sheet-like material W is introduced into the first roll 21 in a continuous state. Then, as described above, the sheet-like material W is severed into individual units of worn articles on the first roll 21 and received on the pad 1 from the first roll 21.

Then, after the attitude of the sheet-like material W of FIG. 4 and the distance between sheet-like materials W are changed by the pad 1, the sheet-like material W is handed over from the pad 1 of FIG. 1B to the second roll 22.

To explain this more in detail, the first roll 21 of FIG. 1B places the severed sheet-like material W on the holding surface 1F of the pad 1 in the first attitude in the high speed section S2 of FIG. 2. The attitude of the sheet-like material W is changed, together with the pad 1, by 90° in the deceleration section S3 of FIG. 2 and FIG. 3A.

After changing the attitude, the sheet-like material W is conveyed at a low speed in the slow speed section S4 and is received on the second roll 22 from the holding surface 1F of the pad 1 as shown in FIG. 1B.

Then, the sheet-like material W is placed on the around-torso portion T on the third roll 23 of FIG. 1B, and a laminate that includes sheet-like materials W placed on the around-torso portions T is severed into units of individual diapers, as shown in FIG. 4, downstream of the third roll 23.

FIG. 5A to FIG. 5C generally show the manufacturing system 200.

The manufacturing system 200 includes a panel group comprising a large number of panels 40. In FIG. 5A to FIG. 5C, for the sake of illustration, the panels 40 are colored in gray.

The panels 40 of the panel group are arranged along a vertical plane and support various rolls, and the like. In this embodiment, one panel 40 rotatably supports the cutter 20 and the first roll 21. Another panel 40 rotatably supports the second roll 22 and the third roll 23.

The panels 40 may be supported by pillars 41.

As shown in FIG. 5B, an opening 42 is formed in the panel group. That is, the opening 42 is defined by a group of panels that are arranged upward and leftward/rightward of the linear motor M.

As shown in FIG. 5A and FIG. 5C, the rail portion R is provided on the front side and on the back side of the panel group so that the pads 1 pass through the opening 42.

The opening may be provided on both sides of the linear motor M. That is, two or more panels with openings may be provided and the linear motor M may be arranged so that the circulating pads 1 pass through the openings in a semi-circular arc-shaped portion of the rail portion R.

FIG. 6 is a plan view showing the orbit of the pads 1 of another embodiment.

In the embodiment of FIG. 6, the loop-shaped rail portion R (FIG. 1) is configured so that the sheet-like material W (FIG. 4) can be handed over at a first position Q1 and a second position Q2, at which the conveying directions are parallel to each other and are in the same direction.

That is, it is configured so that one sheet-like material W, which has been received upstream of the first position Q1, can be handed over at the first position Q1, and another sheet-like material W, which has been received upstream of the first position Q1, can be handed over at the second position Q2.

The specific embodiments set forth above primarily comprise a subject matter configured as follows.

A conveying device 100 for conveying a sheet-like material includes: a rail portion R arranged in a loop shape; a plurality of travelers 10; a linear motor M for circulating the travelers 10 along the rail portion R; and a pad 1 attached to each of the travelers 10, wherein the pad 1 circulates in at least one horizontal plane P while holding the sheet-like material W on the pad 1, thereby conveying the sheet-like material W.

With the configuration described above, the pad conveying the sheet-like material circulates in at least one horizontal plane. Therefore, the pad does not rise in the height direction (vertical direction), and it is possible to suppress the load on the linear motor.

Since the pad circulates along one horizontal plane, it is unlikely for the rail portion to become larger in the height direction.

A preferred embodiment further includes a first roll 21 and a second roll 22, wherein the first roll 21 contacts a holding surface 1F of the pad 1 with the sheet-like material W therebetween while holding the sheet-like material W to place the sheet-like material W on the holding surface 1F, and the second roll 22 contacts the holding surface 1F with the sheet-like material W on the pad 1 therebetween to receive the sheet-like material W from the holding surface 1F.

In this case, the sheet-like material W can be transferred from the first roll 21 to the second roll 22 via the pad 1 of the linear motor M.

A more preferred embodiment further includes a controller C for controlling the travel of the traveler 10, wherein the rail portion R includes an acceleration section S1, a high speed section S2 downstream of the acceleration section S1 and adjacent to the acceleration section S1, a deceleration section S3 downstream of the high speed section S2 and adjacent to the high speed section S2, and a low speed section S4 downstream of the deceleration section S3 and adjacent to the deceleration section S3. The controller C performs the speed control so as to accelerate the traveler 10 in the acceleration section S1, cause the traveler 10 to travel at a constant high speed in the high speed section S2, decelerate the traveler 10 in the deceleration section S3, and cause the traveler 10 to travel at a constant low speed in the low speed section S4.

In this case, the pads 1 attached to the travelers 10 are accelerated/decelerated so that it is possible to change the distance between adjacent pads 1.

In a more preferred embodiment, it is configured so that the first roll 21 places the sheet-like material W on the holding surface 1F in the high speed section S2, and the second roll 22 receives the sheet-like material W from the holding surface 1F in the low speed section S4.

In this case, the sheet-like material W can be placed, from the first roll 21, on the holding surface 1F of the pad 1, moving at a high speed, and the pad 1 then decelerates so that the sheet-like material W can be received on the second roll 22 from the holding surface 1F, moving at a low speed.

In a preferred embodiment, each pad 1 is attached to the traveler 10 so that the pad 1 can change its attitude by rotating around an axis L, which is orthogonal to the one horizontal plane P.

In this case, it is possible to change the attitude of the sheet-like material W while conveying the sheet-like material W on the pad 1 along the horizontal plane.

In a more preferred embodiment, the center of gravity of the pad 1 is set at a position that is away from the axis L so that as the traveler 10 is accelerated/decelerated, an inertial force acts on the pad 1 around the axis L, thus causing the pad 1 to swivel around the axis L.

In this case, as the pad 1 is accelerated/decelerated together with the traveler 10, an inertial force acts that urges the pad 1 to swivel, thereby realizing smooth swivel of the pad 1.

A more preferred embodiment further includes a loop-shaped guide 31 to change and control the attitude of the pad 1 during the circulation, and a guided portion 32 guided in the guide 31.

In this case, it is possible to reliably change the attitude of the pad 1.

In another preferred embodiment, the loop-shaped rail portion R is configured so that the sheet-like material W can be handed over at a first position Q1 and a second position Q2, at which the conveying directions are parallel to each other and are in the same direction.

In this case, it is possible to displace the sheet-like material W in the width direction of the conveying direction.

A manufacturing system 200 for manufacturing a disposable worn article includes a panel group comprising a large number of panels 40 standing along a vertical plane, wherein one or more panels 40 of the panel group support the first roll 21 and the second roll 22, and the rail portion R is provided on the front side and on the back side of the panel group so that the pad 1 passes through an opening 42 provided in the panel group.

In this case, the linear motor can be arranged in the system with a high spatial efficiency.

Any feature illustrated and/or depicted in conjunction with one embodiment or preferred embodiments may be used in the same or similar form in one or more of the other embodiments, and/or may be used in combination with, or in place of, the other embodiments.

While preferred embodiments have been described above with reference to the drawings, obvious variations and modifications will readily occur to those skilled in the art upon reading the present specification.

For example, the sheet-like material conveyed by the conveying device may be a torso portion.

The worn article may be a sanitary napkin, or the like.

Thus, such variations and modifications shall fall within the scope of the present invention as defined by the appended claims.

INDUSTRIAL APPLICABILITY

The present invention is applicable to conveyance of various sheet-like materials.

REFERENCE SIGNS LIST

1: Pad, 1F: Holding surface, 1G: Center of gravity, 10: Traveler, 11: Axis center
20: Cutter, 21: First roll, 22: Second roll, 23: Third roll
31: Guide, 31C: Cam groove, 32: Guided portion (cam follower)
40: Panel, 41: Pillar, 42: Opening
100: Conveying device
200: Disposable worn article manufacturing system
C: Controller
F1: First rotation direction, F2: Second rotation direction
M: Linear motor
R: Rail portion
L: Axis, P: Horizontal plane
S1: (First) acceleration section, S2: High speed section, S3: (First) deceleration section
S4: Low speed section, S5: (Second) acceleration section, S6: Constant speed section
Q1: First position, Q2: Second position
W: Sheet-like material (absorbent body), N: Worn article, T: Around-torso portion

The invention claimed is:

1. A conveying device for conveying a sheet-like material, comprising:
   a rail portion arranged in a loop shape;
   a plurality of travelers;
   a linear motor for circulating the travelers along the rail portion; and
   a pad attached to each of the travelers,
   wherein the pad circulates in at least one horizontal plane while holding the sheet-like material on the pad, thereby conveying the sheet-like material,
   the pad is attached to the respective travelers so that the pad is capable of changing its attitude by rotating around an axis, which is orthogonal to the one horizontal plane, and
   a center of gravity of the pad is set at a position that is away from the axis so that as the respective travelers are accelerated/decelerated, an inertial force acts on the pad around the axis, thus causing the pad to swivel around the axis.

2. The conveying device for conveying a sheet-like material according to claim 1, further comprising:
   a controller for controlling travel of the travelers, wherein:
   the rail portion includes an acceleration section, a high speed section downstream of the acceleration section and adjacent to the acceleration section, a deceleration section downstream of the high speed section and adjacent to the high speed section, and a low speed section downstream of the deceleration section and adjacent to the deceleration section; and
   the controller performs a speed control so as to
   accelerate the travelers in the acceleration section,
   cause the travelers to travel at a constant high speed in the high speed section,
   decelerate the travelers in the deceleration section, and
   cause the travelers to travel at a constant low speed in the low speed section.

3. The conveying device for conveying a sheet-like material according to claim 1, further comprising:
   a first roll and a second roll, wherein:
   the first roll contacts a holding surface of the pad with the sheet-like material therebetween while holding the sheet-like material to place the sheet-like material on the holding surface; and
   the second roll contacts the holding surface with the sheet-like material on the pad therebetween to receive the sheet-like material from the holding surface.

4. The conveying device for conveying a sheet-like material according to claim 3, wherein:
   the first roll places the sheet-like material on the holding surface in the high speed section; and the second roll receives the sheet-like material from the holding surface in the low speed section.

5. The conveying device for conveying a sheet-like material according to claim 1, further comprising:
a loop-shaped guide to change and control an attitude of the pad during the circulation; and
a guided portion guided in the guide.

6. The conveying device for conveying a sheet-like material according to claim 1, wherein:
the loop-shaped rail portion is configured so that the sheet-like material is capable of being handed over at a first position and a second position, at which conveying directions are parallel to each other and are in the same direction.

7. A system for manufacturing a disposable worn article having the conveying device for conveying a sheet-like material according to claim 1, comprising:
a panel group comprising a large number of panels standing along a vertical plane, wherein one or more panels of the panel group support the first roll 21 and the second roll, wherein:
the rail portion is provided on a front side and on a back side of the panel group so that the pad passes through an opening provided in the panel group.

8. The conveying device for conveying a sheet-like material according to claim 2, further comprising:
a first roll and a second roll, wherein:
the first roll contacts a holding surface of the pad with the sheet-like material therebetween while holding the sheet-like material to place the sheet-like material on the holding surface; and
the second roll contacts the holding surface with the sheet-like material on the pad therebetween to receive the sheet-like material from the holding surface.

9. The conveying device for conveying a sheet-like material according to claim 2, further comprising:
a loop-shaped guide to change and control an attitude of the pad during the circulation; and
a guided portion guided in the guide.

10. The conveying device for conveying a sheet-like material according to claim 3, further comprising:
a loop-shaped guide to change and control an attitude of the pad during the circulation; and
a guided portion guided in the guide.

11. The conveying device for conveying a sheet-like material according to claim 4, further comprising:
a loop-shaped guide to change and control an attitude of the pad during the circulation; and
a guided portion guided in the guide.

12. The conveying device for conveying a sheet-like material according to claim 2, wherein:
the loop-shaped rail portion is configured so that the sheet-like material is capable of being handed over at a first position and a second position, at which conveying directions are parallel to each other and are in the same direction.

13. The conveying device for conveying a sheet-like material according to claim 3, wherein:
the loop-shaped rail portion is configured so that the sheet-like material is capable of being handed over at a first position and a second position, at which conveying directions are parallel to each other and are in the same direction.

14. The conveying device for conveying a sheet-like material according to claim 4, wherein:
the loop-shaped rail portion is configured so that the sheet-like material is capable of being handed over at a first position and a second position, at which conveying directions are parallel to each other and are in the same direction.

15. The conveying device for conveying a sheet-like material according to claim 5, wherein:
the loop-shaped rail portion is configured so that the sheet-like material is capable of being handed over at a first position and a second position, at which conveying directions are parallel to each other and are in the same direction.

16. A system for manufacturing a disposable worn article having the conveying device for conveying a sheet-like material according to claim 4, comprising:
a panel group comprising a large number of panels standing along a vertical plane, wherein one or more panels of the panel group support the first roll and the second roll, wherein:
the rail portion is provided on a front side and on a back side of the panel group so that the pad passes through an opening provided in the panel group.

17. A system for manufacturing a disposable worn article having the conveying device for conveying a sheet-like material according to claim 10, comprising:
a panel group comprising a large number of panels standing along a vertical plane, wherein one or more panels of the panel group support the first roll and the second roll, wherein:
the rail portion is provided on a front side and on a back side of the panel group so that the pad passes through an opening provided in the panel group.

18. A system for manufacturing a disposable worn article having the conveying device for conveying a sheet-like material according to claim 11, comprising:
a panel group comprising a large number of panels standing along a vertical plane, wherein one or more panels of the panel group support the first roll and the second roll, wherein:
the rail portion is provided on a front side and on a back side of the panel group so that the pad passes through an opening provided in the panel group.

19. A system for manufacturing a disposable worn article having the conveying device for conveying a sheet-like material according to claim 13, comprising:
a panel group comprising a large number of panels standing along a vertical plane, wherein one or more panels of the panel group support the first roll and the second roll, wherein:
the rail portion is provided on a front side and on a back side of the panel group so that the pad passes through an opening provided in the panel group.

20. A system for manufacturing a disposable worn article having the conveying device for conveying a sheet-like material according to claim 15, comprising:
a panel group comprising a large number of panels standing along a vertical plane, wherein one or more panels of the panel group support the first roll and the second roll, wherein:
the rail portion is provided on a front side and on a back side of the panel group so that the pad passes through an opening provided in the panel group.

* * * * *